(12) United States Patent
Dive et al.

(10) Patent No.: US 7,521,469 B2
(45) Date of Patent: Apr. 21, 2009

(54) PHOSPHINIC AMINO ACID COMPOUNDS

(75) Inventors: Vincent Dive, Palaiseau (FR); Nicolas Jullien, Caluire & Cuire (FR); Elizabeth Scalbert, Paris (FR); Athanasios Yiotakis, Athenes (GR); Anastasios Makaritis, Athenes (GR)

(73) Assignees: Les Laboratoires Servier, Courbevoie Cedex (FR); Commissariat a l'Energie Atomique (CEA), Paris Cedex (FR)

( * ) Notice: Subject to any disclaimer, the term of this patent is extended or adjusted under 35 U.S.C. 154(b) by 91 days.

(21) Appl. No.: 11/885,301

(22) PCT Filed: Feb. 28, 2006

(86) PCT No.: PCT/FR2006/000446

§ 371 (c)(1),
(2), (4) Date: Aug. 28, 2007

(87) PCT Pub. No.: WO2006/092495

PCT Pub. Date: Sep. 8, 2006

(65) Prior Publication Data

US 2008/0153890 A1 Jun. 26, 2008

(30) Foreign Application Priority Data

Mar. 1, 2005 (FR) ................... 05 02043

(51) Int. Cl.
*A61K 31/42* (2006.01)
*C07D 261/06* (2006.01)
(52) U.S. Cl. ................ 514/378; 548/240; 548/247
(58) Field of Classification Search ........... 548/240, 548/247; 514/378
See application file for complete search history.

(56) References Cited

U.S. PATENT DOCUMENTS 5,476,847 A * 12/1995 McKittrick et al. ........... 514/80
6,518,260 B1 2/2003 Fournie-Zaluski et al.

FOREIGN PATENT DOCUMENTS

WO 97/00261 1/1997
WO 98/18803 5/1998

OTHER PUBLICATIONS

Lloyd J., et al. "Solid phase synthesis of phosphinic acid endothelin converting enzyme inhibitors" Bioorganic & Medicinal Chemistry Letters, vol. 6, No. 12, Jun. 18, 1996, p. 1323-1326.

Makaritis, A., et al., "Diastereoselective solution an multipin-based combinatorial array synthesis of a novel class of potent Phosphinic metalloprotease inhibitors" Chemistry—A European Journal, vol. 9, No. 9, p. 2079-2094, 2003.
Chen, H., et al., "Phosphinic derivatives as new dual enkephalin-degrading enzyme inhibitors: synthesis, biological properties, and antinociceptive activities" Journal of Medicinal Chemistry, vol. 43, No. 7, p. 1398-1408, 2000.
International Search Report for PCT/FR2006/000446 of Jul. 18, 2006.
Written opinion of the International Searching Authority for PCT/FR2006/000446 of Sep. 11, 2007.
Chackalamannil S., et al., "Highly potent and selective inhibitors of endothelin converting enzyme" Bioorganic and Mecicinal Chemistry Letters, vol. 6, No. 11, p. 1257-1260, Jun. 1, 1996.
French Preliminary Search Report for FR0502043 of Oct. 12, 2005.

* cited by examiner

*Primary Examiner*—Golam M Shameem
(74) *Attorney, Agent, or Firm*—Hueschen and Sage

(57) ABSTRACT

Compounds of formula (I):

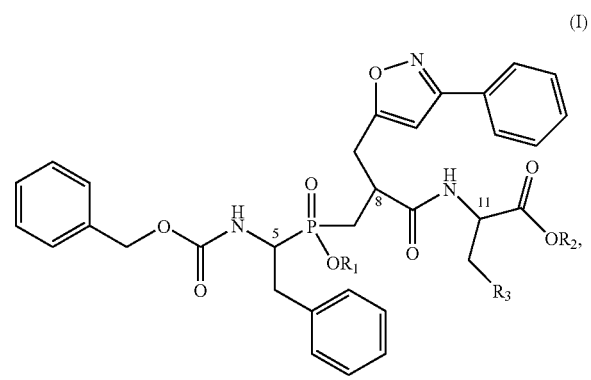

wherein:
$R_1$ represents hydrogen, alkylcarbonyloxyalkyl or alkylcarbonylthioalkyl,
$R_2$ represents hydrogen, alkylcarbonyloxyalkyl, arylcarbonylthioalkyl or optionally substituted arylalkyl,
$R_3$ represents phenyl, which is optionally substituted, or indolyl,
their isomers, and addition salts thereof with a pharmaceutically acceptable acid or base.

Medicinal products containing the same which are useful in the treatment of arterial hypertension and complications thereof.

7 Claims, No Drawings

PHOSPHINIC AMINO ACID COMPOUNDS

The present invention relates to new phosphinic amino acid compounds, to a process for their preparation and to pharmaceutical compositions containing them.

The new phosphinic amino acid compounds according to the invention have the remarkable property of simultaneously inhibiting angiotensin I converting enzyme (ACE) and endothelin converting enzyme (ECE).

The balance that exists between vasoactive peptides—vasoconstrictors (angiotensin II, endothelin-1) on the one hand and vasodilators (natriuretic factors, bradykinin) on the other hand—constitutes an important element in regulating arterial pressure. Synthesis and degradation of those peptides are under the control of various enzymes, amongst which three zinc metalloproteases seem to play a preponderant role:

angiotensin I converting enzyme (ACE), which on the one hand converts angiotensin I, an inactive decapeptide, into angiotensin II, an active octapeptide, and on the other hand degrades bradykinin into inactive peptides, endothelin converting enzyme (ECE), which cleaves big endothelin-1 to form endothelin-1 and seems to participate to a lesser degree in the degradation of bradykinin, neutral endopeptidase (NEP), which inactivates atrial natriuretic peptide (ANP) and bradykinin to form inactive peptides.

Angiotensin II is a vasoconstrictor and antinatriuretic octapeptide. The endothelins are vasoconstrictor and antinatriuretic polypeptides of about twenty amino acids containing two disulphide bridges linking cysteine residues. Bradykinin is a vasodilator and natriuretic nonapeptide.

Angiotensin II, endothelin and bradykinin are the most important polypeptides hitherto considered to be involved in regulating vascular tone, cardiovascular remodelling and hydroelectrolytic homeostasis. Their metabolism is essentially controlled by the three enzymes ACE, ECE and NEP.

Arterial hypertension and also other cardiovascular pathologies are characterised by a disequilibrium in the peptide balance in favour of vasoconstrictor peptides which exert an overall adverse action in the reno-cardiovascular sphere (water and sodium retention, cardiovascular hypertrophy etc.). In spite of the major therapeutic advances made in the 1980s by means of selective ACE inhibitors, the development of new compounds has been found to be necessary in order to improve still further the blood pressure control of hypertensive patients and also their life expectancy (beneficial action on the major cardiovascular risk factors).

The three metalloproteases ACE, ECE and NEP accordingly appear to be promising targets for the treatment of cardiovascular diseases. Therefore, in order to combat the adverse vasoconstrictor effects of angiotensin II and of endothelin-1 and to promote the protective vasodilator effects of ANP and of bradykinin, ACE, NEP and ECE inhibitors have been developed.

Numerous compounds having one or other of those activities are known.

Numerous patent applications describe amino acid compounds that are useful as ACE and ECE inhibitors and useful as mixed ACE/NEP and ECE/NEP inhibitors.

Selective ACE inhibitors which have been used as antihypertensives for some years are described in the patent specification U.S. Pat. No. 4,396,772. The formulae of the compounds described include:

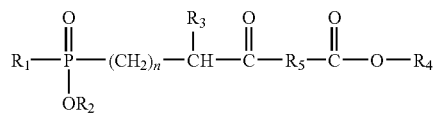

The patent specifications WO 97/32874 and U.S. Pat. No. 5,476,847 describe compounds that are ECE inhibitors. The formulae of the compounds described include:

in patent specification WO 97/32874

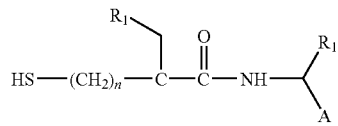

in patent specification U.S. Pat. No. 5,476,847

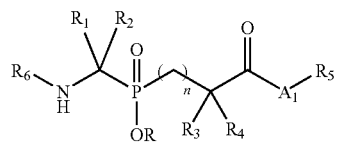

According to the patent application WO 95/35302, certain phosphinic acid compounds having an ECE inhibitory activity useful in the treatment of cardiovascular diseases are known. The formulae of the compounds described include:

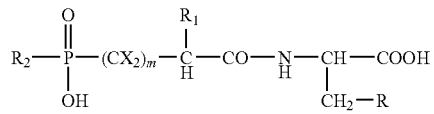

Mixed ACE/NEP inhibitors ("vasopeptidase inhibitor" class) have also been synthesised and clinically tested.

Mixed ACE/NEP inhibitors are described in the patent specifications WO 97/24341, WO 96/22998, WO 93/08142 and EP 0 723 974. The compounds described are sulphurated derivatives of peptides.

In *Bioorganic and Medical Chemistry Letters*, 1996, 6(11), 1257-1260, there are described phosphinic acid compounds having a mixed ACE/NEP inhibitory activity useful in the treatment of cardiovascular diseases. The formulae of those compounds include:

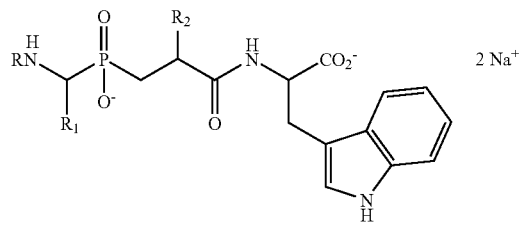

Those compounds have an antihypertensive efficacy that is greater than that of the selective ACE inhibitors. Nevertheless, they have major secondary effects, especially relating to angioedema, very probably associated with an excess of bradykinin (*Trends in Pharmacological Sci.*, 2001, 22, 106-109; *The Lancet*, 2001, 358, 1525-1532). This has resulted in suspension of the clinical development of the furthest advanced mixed ACE/NEP inhibitors such as omapatrilate (*Curr Opin Investig Drugs*, 2001, 2, 1414-1422). The pharmacological properties of the mixed ACE/NEP inhibitors described in the prior art overlook the major cardiovascular role of the endothelin system (*Journal of Hypertension*, 1998, 16(8), 1081-1098) and also the involvement of NEP in the degradation of endothelin-1 (*J. Biol. Chem.*, 1990, 265, 14150-14155). Accordingly, treatment using mixed ACE/NEP inhibitors has the consequence of increasing the level of endothelin-1, which in the long term can prove detrimental to the expected therapeutic benefits.

Finally, mixed ECE/NEP inhibitors are described in *Life Sciences*, 2000, 67(9), 1025-1033 and *Naunyn-Schmiedeberg's Arch. Pharmacol.*, 358 (1, suppl 1): R 513-514 (Abstr). The formulae of those compounds are:

in *Life Sciences*

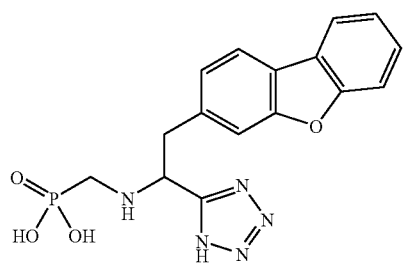

in *Naunyn-Schmiedeberg's Arch. Pharmacol.*

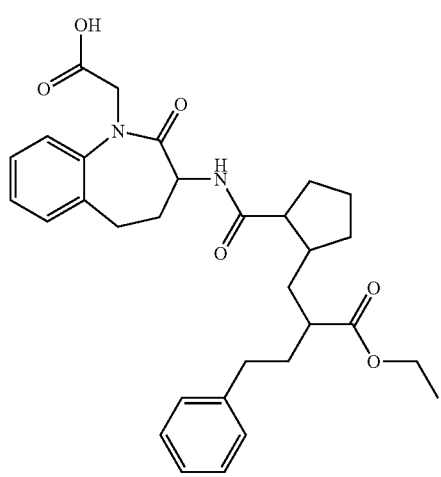

The interest in having mixed ECE/NEP inhibitors is to reduce the level of endothelin whilst increasing the level of natriuretic peptides and accordingly to obtain an additive or synergistic effect which is beneficial for the treatment of cardiovascular and renal diseases.

Nevertheless, because NEP is one of the most important players in the degradation of bradykinin in vivo, the clinical stop put on ACE/NEP inhibitors has also clearly invalidated the development of other multiple inhibitors of vasopeptidases including combining inhibition of NEP, namely mixed ECE/NEP or triple ECE/ACE/NEP inhibitors.

On the other hand, the alternative of mixed ACE/ECE inhibitors remains promising, allowing the expectation of increased cardiovascular efficacy and good safety of use. Such compounds should make it possible to reduce the formation of the two potent vasoconstrictor peptides, angiotensin II and endothelin-1, and to increase levels of bradykinin to a reasonable degree.

It is moreover interesting to note that, although the angiotensin and endothelin systems do function independently, they also function interactively. This "crosstalk" between the two systems has been studied on the experimental level and also on the clinical level. The role of endothelin-1 as a mediator of certain cardiovascular effects of angiotensin II has very particularly been explored (*Hypertension*, 1997, 30, 29-34; *Cardiovasc. Res.*, 1999, 43, 300-307; *Hypertension*, 2002, 40, 840-846; *Clin. Exp. Pharmacol. Physiol.*, 2003, 30, 278-283; *Hypertension*, 2002, 39, 715-720; *Hypertension*, 2003, 42, 825-830; *Bioorg Med Chem. Letters*, 2003, 13, 1093-1096).

Overall, the data obtained suggest that inhibition of one of those systems gives rise to hyperactivity of the other system, which favours the "mixed inhibition" approach in order to reinforce the therapeutic potential of each of those properties, whilst avoiding counter-regulation.

Finally, evidence for the mixed ACE/ECE inhibition concept, that is to say the therapeutic benefit expected for that approach, has hitherto been analysed on the experimental level, in three therapeutic directions: arterial hypertension, cardiac insufficiency and renal protection. Evidence for the concept has generally been provided by combining two selective compounds: on the one hand, a selective ACE inhibitor or an angiotensin II $AT_1$ receptor blocker for blocking the angiotensin system and, on the other hand, an endothelin-1 $ET_A$ receptor blocker or a mixed endothelin-1 $ET_A/ET_B$ receptor blocker or, in rare cases, an ECE inhibitor for endothelin blocking.

The literature broadly supports the concept. The therapeutic benefits are demonstrated in animals either on the structural level or on the functional level in arterial hypertension (*J Cardiovasc Pharmacol.*, 2000, 36, S337-S341; *Clin Sci.*, 2002, 103, 363S-366S; *Am J Hypertens.*, 2003, 16, 324-328) and cardiac insufficiency (*Cardiovasc. Res.*, 2002, 54, 85-94; *Circulation*, 2002, 106, 1159-1164). Protection of certain target organs such as the kidney and brain is strongly anticipated (*J. Am. Soc. Nephrol.*, 2001, 12, 2572-2584).

The clinical reflection of all those preclinical results could be a greater number of patients normalised by the mixed treatment. It is probable that the "blood pressure" benefit will, in the long term, be complemented by better protection of the target organs of arterial hypertension (i.e. prevention of "target organ damage" at the cardiovascular, renal and cerebral levels) and also by favourable effects on certain risk factors, thereby preventing complications of arterial hypertension.

The present invention has the aim of providing new compounds which behave as mixed ACE/ECE inhibitors without exerting any inhibition on NEP.

The compounds of the present invention are accordingly very effective in the treatment of arterial hypertension and complications thereof including pulmonary arterial hypertension, myocardial ischaemia, angina pectoris, cardiac insufficiency, vasculopathies, nephropathies, diabetic retinopathies, atherosclerosis and post-angioplasty restenosis, acute or chronic renal insufficiency, cerebrovascular diseases including stroke and subarachnoid haemorrhage, and peripheral ischaemia.

More specifically, the present invention relates to compounds of formula (I):

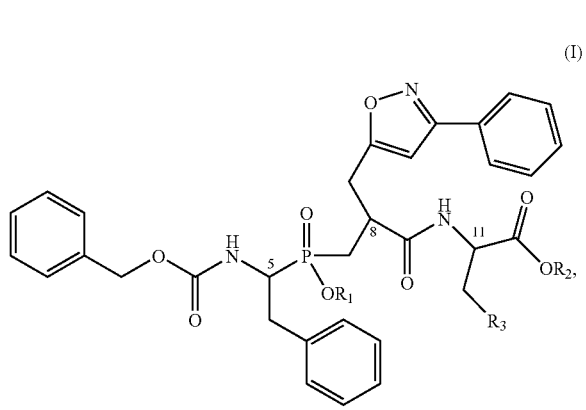

wherein:
- R₁ represents a hydrogen atom or a group selected from $(C_1\text{-}C_6)$alkyl-carbonyloxy-$(C_1\text{-}C_6)$alkyl, it being possible for each alkyl moiety to be linear or branched, and $(C_1\text{-}C_6)$alkyl-carbonylthio-$(C_1\text{-}C_6)$alkyl, it being possible for each alkyl moiety to be linear or branched,
- R₂ represents a hydrogen atom or a group selected from $(C_1\text{-}C_6)$alkyl-carbonyloxy-$(C_1\text{-}C_6)$alkyl, it being possible for each alkyl moiety to be linear or branched, arylcarbonylthio-$(C_1\text{-}C_6)$alkyl, it being possible for the alkyl moiety to be linear or branched, and aryl-$(C_1\text{-}C_6)$alkyl, it being possible for the alkyl moiety to be linear or branched and the aryl moiety of which is optionally substituted by a $(C_1\text{-}C_6)$alkyl-carbonyloxy group,
- R₃ represents a phenyl group optionally substituted by a hydroxy group or R₃ represents a 3-indolyl group, or

- R₁ can also represent a linear or branched $(C_1\text{-}C_6)$alkyl group, R₂ represents a linear or branched $(C_1\text{-}C_6)$alkyl group, when R₃ represents a phenyl group substituted by a hydroxy group, to their enantiomers and diastereoisomers, and also to addition salts thereof with a pharmaceutically acceptable base, and to hydrates and solvates thereof.

Among the pharmaceutically acceptable bases there may be mentioned, without implying any limitation, sodium hydroxide, potassium hydroxide, triethylamine, tert-butylamine etc.

According to an advantageous embodiment of the invention, preferred compounds are compounds wherein R₁ and R₂ each represent a hydrogen atom.

According to a second advantageous embodiment of the invention, preferred compounds are compounds wherein R₁ represents a hydrogen atom and R₃ represents a phenyl group substituted by a hydroxy group.

According to a third advantageous embodiment of the invention, preferred compounds are compounds wherein R₂ represents a hydrogen atom and R₃ represents a phenyl group substituted by a hydroxy group.

Among preferred compounds of the invention there may be mentioned more specifically:
(5R,8R,11S)-5-benzyl-6-hydroxy-11-(1H-indol-3-ylmethyl)-3,9-dioxo-1-phenyl-8-[(3-phenyl-5-isoxazolyl)methyl]-2-oxa-4,10-diaza-6-phosphadodecan-12-oic acid 6-oxide,
(5R,8R,11S)-5,11-dibenzyl-6-hydroxy-3,9-dioxo-1-phenyl-8-[(3-phenyl-5-isoxazolyl)methyl]-2-oxa-4,10-diaza-6-phosphadodecan-12-oic acid 6-oxide,
(5R,8R,11S)-5-benzyl-6-hydroxy-11-(4-hydroxybenzyl)-3,9-dioxo-1-phenyl-8-[(3-phenyl-5-isoxazolyl)methyl]-2-oxa-4,10-diaza-6-phosphadodecan-12-oic acid 6-oxide.

The enantiomers, diastereoisomers, and addition salts with a pharmaceutically acceptable base, of the preferred compounds form an integral part of the invention.

The present invention relates also to a process for the preparation of compounds of formula (I), which process is characterised in that there is used, as starting material, diphenylmethanamine chloride, which is reacted with phenylacetaldehyde in the presence of phosphinic acid, $H_3PO_2$, and hydrochloric acid to yield the compound of formula (II):

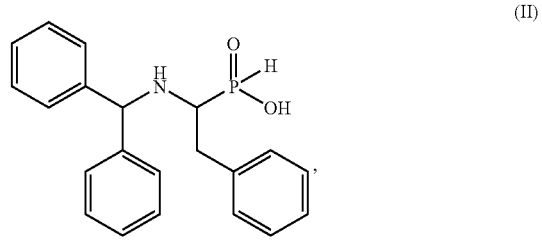

which compound of formula (II) is subjected to the action of aqueous hydrobromic acid to yield the compound of formula (III):

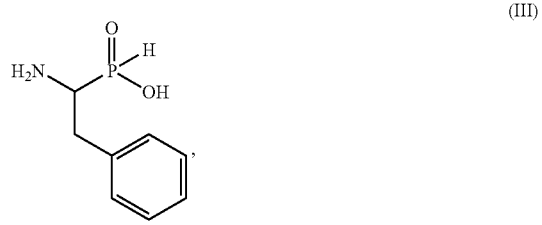

which compound of formula (III) is reacted with benzyl chloroformate in a basic medium to yield the compound of formula (IV):

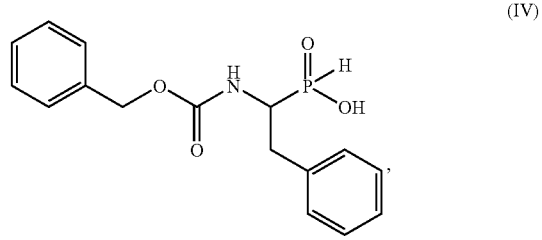

which compound of formula (IV) is placed in the presence of R-(+)-N,N-(phenyl)(ethyl)-amine and then subjected to the action of hydrochloric acid to yield the compound of formula (R-IV), the R enantiomer of the compound of formula (IV):

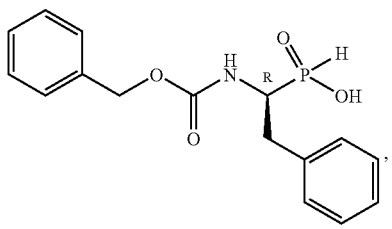

(R-IV)

which compound of formula (R-IV) is reacted, in the presence of 1,1,1,3,3,3-hexamethyldisilazane, with a compound of formula (V):

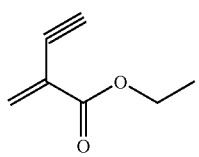

(V)

to yield the compound of formula (R-VI):

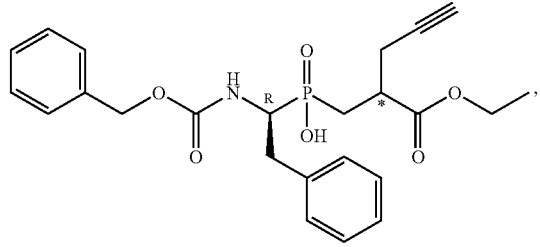

(R-VI)

which compound of formula (R-VI) is reacted with a solution of sodium hydroxide to yield the compound of formula (R-VII):

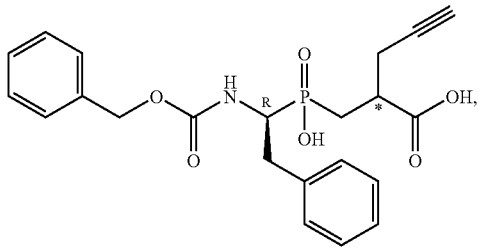

(R-VII)

which compound of formula (R-VII) is subjected:
1) either, in the presence of diisopropylethylamine, 1-hydroxybenzotriazole and 1-ethyl-3-[3-(dimethylamino)propyl]carbodiimide chloride, to the action of a compound of formula (VIII):

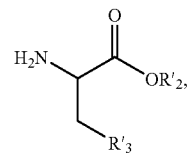

(VIII)

wherein $R'_2$ represents a linear or branched ($C_1$-$C_6$)alkyl group and $R'_3$ represents a group selected from phenyl (optionally substituted by a linear or branched ($C_1$-$C_6$) alkoxy group) and 3-indolyl, to yield the compound of formula (R,S-IX):

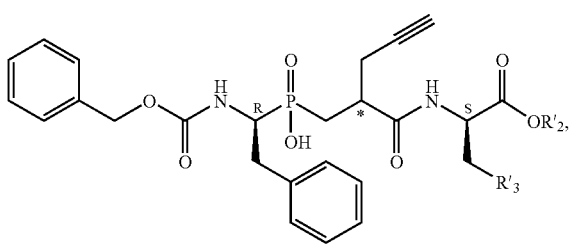

(R,S-IX)

wherein $R'_2$ and $R'_3$ are as defined hereinbefore, which compound of formula (R,S-IX) is reacted with benzaldoxime in the presence of N-chlorosuccinimide in a basic medium to yield the compound of formula (R,S-X):

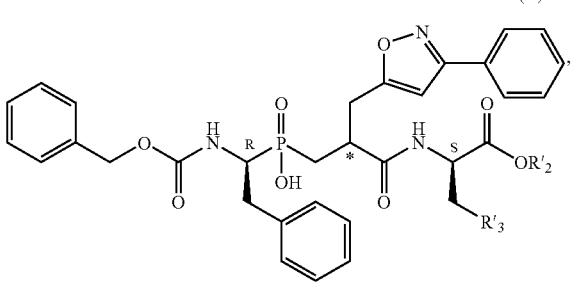

(R,S-X)

wherein $R'_2$ and $R'_3$ are as defined hereinbefore, which compound of formula (R,S-X) is placed in an acid medium to yield the compound of formula (I/a), a particular case of the compounds of formula (I):

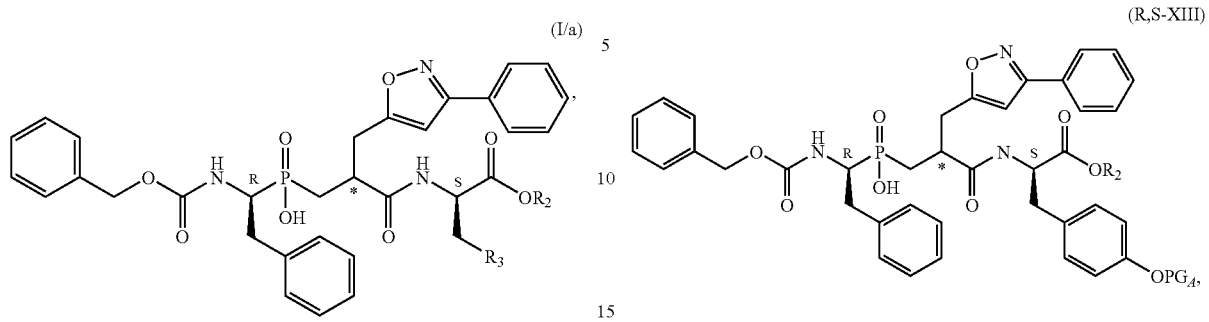

wherein $R_2$ and $R_3$ are as defined for formula (I), 2) or to the same conditions as the compound of formula (R,S-IX) to yield the compound of formula (R-XI):

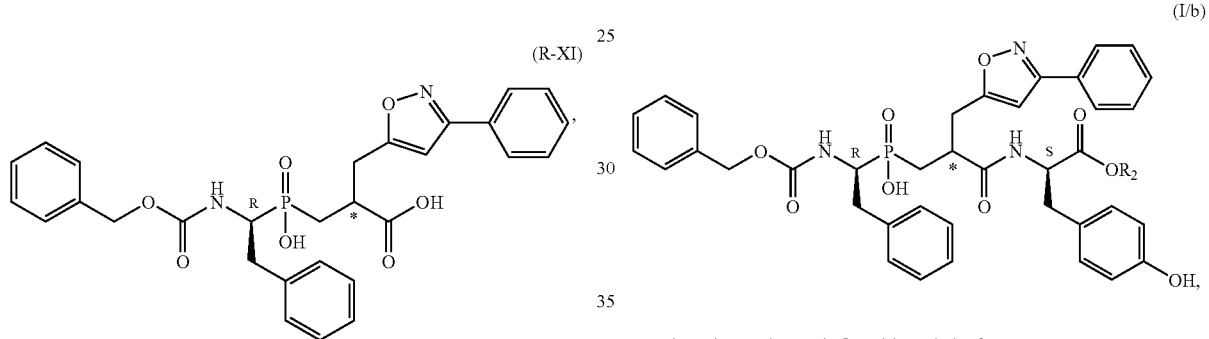

which compound of formula (R-XI) is subjected:

A/ either, in the presence of diisopropylethylamine, 1-hydroxybenzotriazole and 1-ethyl-3-[3-(dimethylamino)propyl]carbodiimide chloride, to the action of a compound of formula (XII):

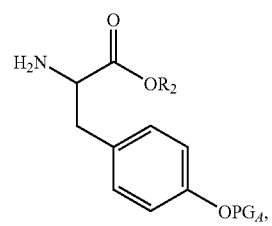

wherein $R_2$ is as defined hereinbefore and $PG_A$ represents a protecting group for the phenol function (T. W. Greene, "*Protective Group in Organic Synthesis*", Wiley-Interscience, New-York, 1981) well known to the person skilled in the art, to yield the compound of formula (R,S-XIII):

(R,S-XIII)

wherein $R_2$ and $PG_A$ are as defined hereinbefore, the phenol function of which compound of formula (R,S-XIII) is deprotected by customary techniques of organic chemistry well known to the person skilled in the art to yield the compound of formula (I/b), a particular case of the compounds of formula (I):

(I/b)

wherein $R_2$ is as defined hereinbefore,

B/ or to the action of a compound of formula (XIV) under the same conditions as hereinbefore:

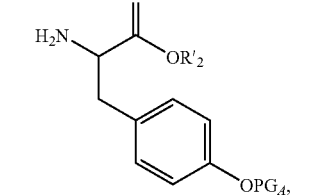

wherein $R'_2$ and $PG_A$ are as defined hereinbefore,
to yield the compound of formula (R,S-XV):

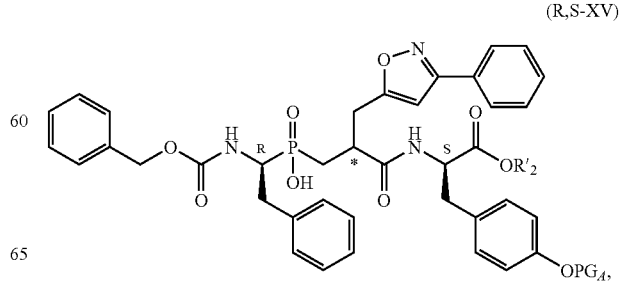

wherein $R_2$ and $PG_A$ are as defined hereinbefore,
which compound of formula (R,S-XV) is subjected:
α) either, in the presence of sodium iodide, $(nBu)_4NHSO_4$ and triethylamine, to the action of a compound of formula (XVI):

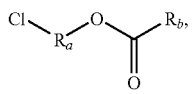
(XVI)

wherein $R_a$ and $R_b$ each independently of the other represents a linear or branched $(C_1-C_6)$alkyl group,
to yield the compound of formula (R,S-XVII):

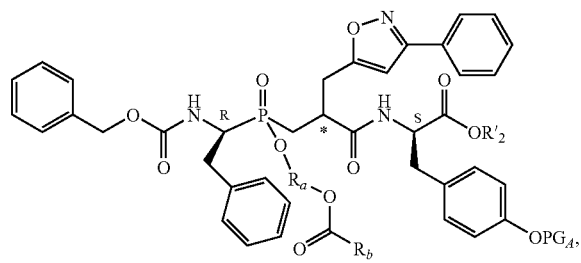
(R,S-XVII)

wherein $R_a$, $R_b$, $R'_2$ and $PG_A$ are as defined hereinbefore,
β) or, in the presence of PyBOP and diisopropylethylamine, to the action of a compound of formula (XVIII):

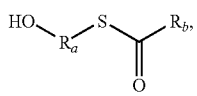
(XVIII)

wherein $R_a$ and $R_b$ are as defined hereinbefore,
to yield the compound of formula (R,S-XIX):

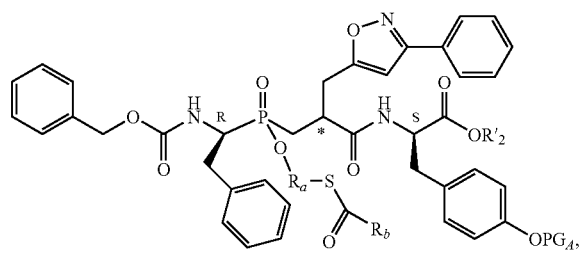
(R,S-XIX)

wherein $R_a$, $R_b$, $R'_2$ and $PG_A$ are as defined hereinbefore,
the compounds of formulae (R,S-XVII) and (R,S-XIX) constituting the compound of formula (R,S-XX):

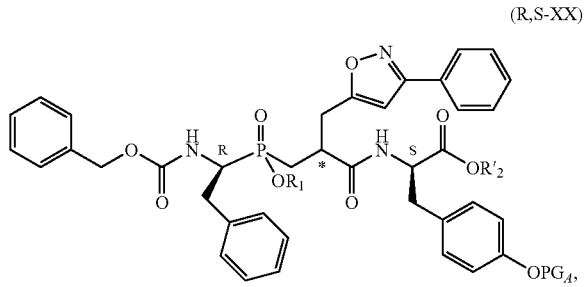
(R,S-XX)

wherein $R_1$ is as defined for formula (I), and $R'_2$ and $PG_A$ are as defined hereinbefore,
the phenol function and carboxylic acid function of which compound of formula (R,S-XX) are deprotected by customary techniques of organic chemistry well known to the person skilled in the art to yield the compound of formula (I/c), a particular case of the compounds of formula (I):

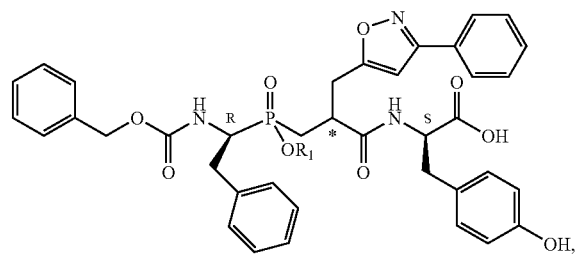
(I/c)

wherein $R_1$ is as defined hereinbefore,
which compounds of formulae (I/a), (I/b) and (I/c) are separated, if desired, into their stereoisomers by conventional separation techniques, are purified, where necessary, by conventional purification techniques and are converted, if desired, into their addition salts with a pharmaceutically acceptable base.

The compound of formula (XII):

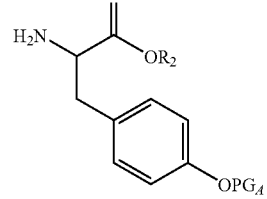
(XII)

can be obtained starting from a compound of formula (XXI):

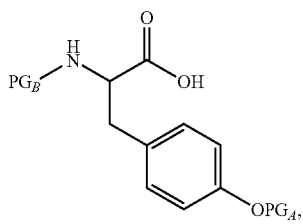

wherein $PG_A$ is as defined hereinbefore and $PG_B$ represents a protecting group for the amine function (T. W. Greene, "*Protective Group in Organic Synthesis*", Wiley-Interscience, New-York, 1981) well known to the person skilled in the art, which compound of formula (XXI) is reacted:
a) either, in the presence of NaI, $(nBu)_4NHSO_4$ and $NEt_3$, with a compound of formula (XXII):

wherein $R_2$ is as defined hereinbefore, to yield the compound of formula (XXIII):

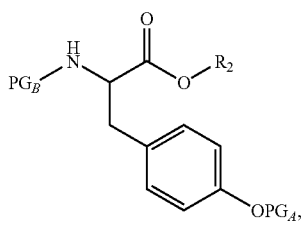

wherein $PG_A$, $PG_B$ and $R_2$ are as defined hereinbefore,
b) or, in the presence of EDC.HCl and 4-dimethyl-aminopyridine, with a compound of formula (XXIV):

wherein $R_2$ is as defined hereinbefore,
to yield the compound of formula (XVIII) as defined hereinbefore,
the amine function of which compound of formula (XXIII) is deprotected according to customary techniques of organic synthesis well known to the person skilled in the art.

The present invention relates also to pharmaceutical compositions comprising compounds of formula (I) in combination with one or more pharmaceutically acceptable excipients.

Among the pharmaceutical compositions according to the invention there may be mentioned more especially those that are suitable for oral, parenteral, nasal, per- or trans-cutaneous, rectal, perlingual, ocular or respiratory administration, and especially tablets or dragées, sublingual tablets, sachets, paquets, gelatin capsules, glossettes, lozenges, suppositories, creams, ointments, dermal gels, and injectable or drinkable ampoules.

The useful dose varies according to the sex, age and weight of the patient, the administration route, the nature of the therapeutic indication and any associated treatments and ranges from 0.1 mg to 1 g per 24 hours, in one or more administrations.

The Examples that follow illustrate the invention, without limiting it in any way. The Preparations that follow result in compounds of the invention or in synthesis intermediates of use in preparation of the invention.

The starting materials used are commercial products or are prepared according to known methods of preparation.

The structures of the compounds described in the Examples were determined according to customary spectrophotometric techniques (infra-red, NMR, mass spectrometry).

A (5R,8*,11S) compound is understood to mean a racemic mixture of 2 diastereoisomers having the absolute configurations (5R,8S,11S) and (5R,8R,11S).

Preparation 1: Ethyl 2-methylene-4-pentynoate 34.9 g of diethyl malonate are slowly added to a solution of EtONa prepared by dissolution of 5.0 g of sodium in 280 ml of absolute ethanol. The reaction mixture is heated at 50° C. for 1 hour, and then 38.8 ml of 3-bromo-1-propyne in 100 ml of absolute ethanol are added dropwise to the mixture. The reaction mixture is stirred for 12 hours at that temperature. After evaporation under reduced pressure, the residue is taken up in diethyl ether and extracted with water. The organic phase is dried over sodium sulphate, filtered and then evaporated under reduced pressure. The oil obtained is taken up in 100 ml of absolute ethanol and then a solution of KOH (12.2 g in 340 ml of ethanol) is added dropwise. After stirring at ambient temperature for 1.5 hours, the ethanol is evaporated off under reduced pressure, and the residue is dissolved in water and extracted with diethyl ether. The aqueous phase is cooled with the aid of an ice bath, acidified with 2M HCl to pH~1 and extracted with diethyl ether. The organic phase is dried over sodium sulphate, filtered and then evaporated under reduced pressure. 35.0 ml of pyridine, 13.4 g of paraformaldehyde and 1.85 ml of piperidine are added to the residue obtained, and the reaction mixture is stirred at 100-105° C. for 3 hours. After cooling to ambient temperature, the mixture is diluted with 400 ml of diethyl ether and the organic phase is successively washed with water, 2M HCl, 5% $NaHCO_3$ solution and saturated NaCl solution. The organic phase is dried over sodium sulphate, filtered and then evaporated under reduced pressure. Chromatography over silica gel (petroleum ether (40-60° C.)/diethyl ether: 9.5/0.5 to 8/12) allows the expected product to be isolated.

$R_f$=0.31 (petroleum ether (40-60° C.)/diethyl ether: 9.5/0.5)

Preparation 2: 2-{[(1R)-1-{[(Benzyloxy)carbonyl]amino}-2-phenylethyl)(hydroxy)-phosphoryl]methyl}-4-pentynoic acid Step A:
1-(Benzhydrylamino)-2-phenylethylphosphinic acid 51.5 ml of a 50% aqueous solution of $H_3PO_2$ are added to a suspension of 109.5 g of diphenylmethanamine chloride in 750 ml of ethanol 90%, and then the reaction mixture is heated to 85-90° C. At that temperature, 58.4 ml of phenylacetaldehyde in 175 ml of ethanol are added over a period of 3 hours, and heating is continued for 3 more hours, followed by stirring for 16 hours at ambient temperature. The precipitate that is formed is filtered off, washed with cold ethanol and with diethyl ether and then dried, thereby allowing the expected product to be isolated.

Step B: 1-Amino-2-phenylethylphosphinic acid 181.1 g of the compound of Step A above in 500 ml of hydrobromic acid are heated at 110-120° C. for 2 hours. The mixture is then concentrated under reduced pressure, and the residue is diluted with water and extracted with diethyl ether. The aqueous phase is concentrated and 600 ml of absolute ethanol are added to the residue. 60 ml of previously cooled propylene oxide are slowly added to the reaction mixture, which is held at 0° C. The expected product which precipitates out on cooling is filtered off, washed with diethyl ether and then dried.

Step C: 1-{[(Benzyloxy)carbonyl]amino}-2-phenylethlylphosphinic acid 110 ml of a 4M sodium hydroxide solution are added to a suspension of 49.4 g of the compound of Step B above in 120 ml of water. The reaction mixture is brought to 0° C., and then 45.5 ml of benzyl chloroformate are added over a period of 1 hour. The mixture is stirred at 0° C. for 1 hour and at ambient temperature for 4 hours whilst bringing the pH of the solution to 9-10 by adding 2M sodium hydroxide solution. The mixture is then stirred at ambient temperature overnight and is then extracted with diethyl ether. The aqueous phase is acidified by the addition of 6M hydrochloric acid. The expected product precipitates out, is filtered off, washed with water and with diethyl ether and is then dried over $P_2O_5$.

Step D: (1R)-1-{[(Benzyloxy)carbonyl]amino}-2-phenylethylphosphinic acid

A solution of 83.4 g of the compound of Step C above in 1000 ml of absolute ethanol is heated at reflux. A solution of 34.4 ml of R-(+)-N,N-(phenyl)(ethyl)amine in 170 ml of ethanol is slowly added to the reaction mixture. After 15 minutes, the reaction mixture is brought to ambient temperature and cooled at 4° C. overnight. The precipitate formed is filtered off and washed with absolute ethanol and with diethyl ether. The solid is recrystallised from 445 ml of absolute ethanol. The salt obtained is suspended in 300 ml of 6M hydrochloric acid and is stirred for 2-3 hours. The solid is filtered off, washed with $H_2O$ and with $Et_2O$, and is then dried over $P_2O_5$.

Optical rotation $[\alpha]_{20}^D = -46.7°$ (1% in absolute ethanol)

Step E: (1R)-1-{[(Benzyloxy)carbonyl]amino}-2-phenylethyl-[2-(ethoxycarbonyl)-4-pentynyl]phosphinic acid 1.3 mmol of the compound of Preparation 1 are added dropwise to a mixture of 1 mmol of the compound of Step D above and 5 mmol of HMDS heated at 110° C. for 1 hour under an argon atmosphere. The reaction mixture is heated at 100-105° C. for 3 more hours. It is then cooled to 70° C., and absolute ethanol is added in small portions still under an argon atmosphere. Stirring is continued for a further 15 minutes at that temperature. The solvent is then evaporated off under reduced pressure. Chromatography over silica gel (chloroform/methanol/acetic acid: 7/0.3/0.3) allows the expected product to be isolated.

Step F: 2-{[((1R)-1-{[(Benzyloxy)carbonyl]amino}-2-phenylethyl)(hydroxy)-phosphoryl]methyl}-4-pentynoic acid A solution of 1 mmol of the compound of Step E above in 9 ml of ethanol is cooled to 0° C. 5-6 mmol of IM sodium hydroxide are added in small portions, and then the reaction mixture is stirred at ambient temperature for 6-8 hours. After acidification with 2M HCl, the ethanol is evaporated off, and the residue is taken up in water and extracted with ethyl acetate. The organic phase is washed with water and with saturated sodium chloride solution and is then dried over sodium sulphate and evaporated under reduced pressure. The expected product is obtained by precipitating from a diethyl ether/petroleum ether mixture.

Preparation 3: 3-[((1R)-1-{[(Benzyloxy)carbonyl]amino}-2-phenylethyl)(hydroxy)-phosphoryl]-2-[(3-phenyl-5-isoxazolyl)methyl]propanoic acid

Step A: 2-{[((1R)-1-{[(Benzyloxy)carbonyl]amino}-2-phenylethyl)(hydroxy)-phosphoryl]methyl}-4-pentynoic acid This compound is obtained in accordance with a procedure described in the literature (A. Makaritis et al., Chem. Eur. J., 2003, 9, 2079-2094).

Step B: 3-[((1R)-1-{[(Benzyloxy)carbonyl]amino}-2-phenylethyl)(hydroxy)-phosphoryl]-2-[(3-phenyl-5-isoxazolyl)methyl]propanoic acid 1,3-Dipolar cycloaddition is carried out on the compound of Step A above using benzaldehyde oxime, in accordance with a procedure described in the literature (A. Makaritis et al., Chem. Eur. J., 2003, 9, 2079-2094).

EXAMPLE 1

(5R,8R,11S)-5-Benzyl-6-hydroxy-11-(1H-indol-3-ylmethyl)-3,9-dioxo-1-phenyl-8-[(3-phenyl-5-isoxazolyl)methyl]-2-oxa-4,10-diaza-6-phosphadodecan-12-oic acid 6-oxide

Step A: (1R)-1-{[(Benzyloxy)carbonyl]amino}-2-phenylethyl-[2-({[(1S)-1-(1H-indol-3-ylmethyl)-2-methoxy-2-oxoethyl]amino}carbonyl)-4-pentynyl]phosphinic acid To a suspension of 1 mmol of the compound of Preparation 2 in 20 ml of dichloromethane there are added 3 mmol of diisopropylethylamine, 1 mmol of 1-tryptophan methyl ester chloride, 1 mmol of HOBt and 4 mmol of EDC.HCl. The reaction mixture is stirred for 2 hours at ambient temperature and is then diluted with dichloromethane. 1M hydrochloric acid is then added to form two phases. The organic phase is washed with 1M HCl, dried over sodium sulphate and then concentrated under reduced pressure. The expected product is obtained by precipitation from a diethyl ether/petroleum ether mixture.

Step B: (1R)-1-{[(Benzyloxy)carbonyl]amino}-2-phenylethyl-{3-{[(1S)-1-(1H-indol-3-ylmethyl)-2-methoxy-2-oxoethyl]amino}-3-oxo-2-[(3-phenyl-4-isoxazolyl)methyl)]propyl}phosphinic acid 6 mmol of benzaldoxime are dissolved in 5 ml of chloroform, and 2 drops of pyridine are added to the solution. 6 mmol of N-chlorosuccinimide are then added and, after stirring for 10 minutes at ambient temperature, the reaction mixture is stirred at 45° C. for 3-4 hours. 1 mmol of the compound of Step A above is then added, as well as 7 mmol of triethylamine. The reaction mixture is stirred at 45° C. for 96 hours and is then concentrated under reduced pressure, and the residue is taken up in ethyl acetate and washed with 1M HCl and with saturated sodium chloride solution. The organic phase is dried over sodium sulphate and concentrated under reduced pressure. The expected product is obtained by precipitation from a diethyl ether/petroleum ether mixture.

Step C: (5R,8*,11S)-5-Benzyl-6-hydroxy-11-(1H-indol-3-ylmethyl)-3,9-dioxo-1-phenyl-8-[(3-phenyl-4-isoxazolyl)methlyl)]-2-oxa-4,10-diaza-6-phosphadodecan-12-oic acid 6-oxide The product is obtained according to the procedure of Step F of Preparation 1, using the compound of Step B above instead of the compound of Step E.

Step D: (5R,8R,11S)-5-Benzyl-6-hydroxy-11-(1H-indol-3-ylmethyl)-3,9-dioxo-1-phenyl-8-[(3-phenyl-4-isoxazolyl)methyl)]-2-oxa-4,10-diaza-6-phosphadodecan-12-oic acid 6-oxide The (R,R,S) diastereoisomer was obtained by purification of the compound of Step C above in isocratic mode with a buffer composed of 40% acetonitrile and 60% 83.3 mM ammonium formate at pH 6.4, using a 250×30 mm AIT column (stationary phase Kromasil $C_{18}$ beads of 5 μm, pores 100 Å).
Mass spectrometry (ES/MS)=733.2 Da

EXAMPLE 2

(5R,8R,11S)-5,11-Dibenzyl-6-hydroxy-3,9-dioxo-1-phenyl-8-[(3-phenyl-5-isoxazolyl)methyl]-2-oxa-4,10-diaza-6-phosphadodecan-12-oic acid 6-oxide

Step A: 2-({[(1S)-1-Benzyl-2-tert-butoxy-2-oxoethyl]amino}carbonyl)-4-pentynyl-((1R)-1-{[(benzyloxy)carbonyl]amino}-2-phenylethyl)-phosphinic acid This compound is obtained according to the procedure described in Step A of Example 1, using L-phenylalanine O-di-tert-butyl ester chloride instead of 1-tryptophan methyl ester chloride.

Step B: 3-({[(1S)-1-Benzyl-2-tert-butoxy-2-oxoethyl]amino}-3-oxo-2-[(3-phenyl-5-isoxazolyl)methyl]propyl((1R)-1-{[(benzyloxy)carbonyl]amino}-2-phenyl-ethyl)-phosphinic acid This compound is obtained according to the procedure described in Step B of Example 1, using the compound of Step A above. The product is purified by chromatography on silica gel (chloroform/methanol/acetic acid: 7/0.3/0.3).

Step C: (5R,8*,11S)-5,11-Dibenzyl-6-hydroxy-3,9-dioxo-1-phenyl-8-[(3-phenyl-5-isoxazolyl)methyl]-2-oxa-4,10-diaza-6-phosphadodecan-12-oic acid 6-oxide The product is obtained by reacting the compound of Step B above with trifluoroacetic acid, triisopropylamine, dichloromethane and water in the proportions 85/2.5/10/2.5.

Step D: (5R,8R,11S)-5,11-Dibenzyl-6-hydroxy-3,9-dioxo-1-phenyl-8-[(3-phenyl-5-isoxazolyl)methyl]-2-oxa-4,10-diaza-6-phosphadodecan-12-oic acid 6-oxide The (R,R,S) diastereoisomer was obtained by purification of the compound of Step C above in isocratic mode using a semi-preparative 250×10 mm AIT column (stationary phase Kromasil $C_{18}$ beads of 10 μm, pores 100 Å). Isocratic elution under acid conditions: 52% acetonitrile; 0.1% trifluoroacetic acid.
Mass spectrometry (ES/MS)=694.3 Da

EXAMPLE 3

(5R,8R,11S)-5-Benzyl-6-hydroxy-11-(4-hydroxybenzyl)-3,9-dioxo-1-phenyl-8-[(3-phenyl-5-isoxazolyl)methyl]-2-oxa-4,10-diaza-6-phosphadodecan-12-oic acid 6-oxide

Step A: (1R)-1-{[(Benzyloxy)carbonyl]amino}-2-phenylethyl-[2-({[(1S)-2-tert-butoxy-1-(4-tert-butoxybenzyl)-2-oxoethyl]amino}carbonyl)-4-pentynyl]phosphinic acid This compound is obtained according to the procedure described in Step A of Example 1, using L-tyrosine O-di-tert-butyl ester chloride instead of 1-tryptophan methyl ester chloride.

Step B: (1R)-1-{[(Benzyloxy)carbonyl]amino}-2-phenylethyl-{3-{[(1S)-2-tert-butoxy-1-(4-tert-butoxybenzyl)-2-oxoethlyl]amino}-3-oxo-2-[(3-phenyl-5-isoxazolyl)-methyl]propyl}phosphinic acid This compound is obtained according to the procedure described in Step B of Example 2, using the compound of Step A above.

Step C: (5R,8*,11S)-5-Benzyl-6-hydroxy-11-(4-hydroxybenzyl-3,9-dioxo-1-phenyl-8[(3-phenyl-5-isoxazolyl)methyl]-2-oxa-4,10-diaza-6-phosphadodecan-12-oic acid 6-oxide This compound is obtained according to the procedure described in Step C of Example 3, using the compound of Step B above.

Step D: (5R,8R,11S)-5-Benzyl-6-hydroxy-11-(4-hydroxybenzyl)-3,9-dioxo-1-phenyl-8-[(3-phenyl-5-isoxazolyl)methyl]-2-oxa-4,10-diaza-6-phosphadodecan-12-oic acid 6-oxide The (R,R,S) diastereoisomer was obtained by purification of the compound of Step C above in isocratic mode using a semi-preparative 250×10 mm AIT column (stationary phase Kromasil $C_{18}$ beads of 10 µm, pores 100 Å). Isocratic elution under acid conditions: 43% acetonitrile; 0.1% trifluoroacetic acid.

Mass spectrometry (ES/MS)=711.3 Da

EXAMPLE 4

(5R,8*,11S)-5-Benzyl-11-(4-hydroxybenzyl)-3,9,12,16-tetraoxo-1-phenyl-8-[(3-phenyl-5-isoxazolyl)methyl]-2,13,15-trioxa-4,10-diaza-17,17-dimethyloctadecane-6-phosphinic acid Step A: N-[(Benzyloxy)carbonyl]-4-[(tert-butoxycarbonyl)oxy]phenylalanine Potassium hydroxide is added to a solution of 10 mmol of N-[(benzyloxy)carbonyl]-4-hydroxyphenylalanine until a pH of 12 is reached. The reaction mixture is cooled in an ice bath, and 1.5 equivalents of $Boc_2O$ are added, and the mixture is then returned to ambient temperature whilst maintaining the pH of the solution at 12 by addition of solid potassium hydroxide. After 2 hours, a further 0.5 of an equivalent of $Boc_2O$ is added. After 18 hours, the mixture is then concentrated under reduced pressure and the aqueous phase is extracted with a mixture (1/1) of $Et_2O$/petroleum ether. The aqueous phase is acidified in the cold state with 2M HCl until a pH of 1 is reached, and is then extracted twice with ethyl acetate. Chromatography (chloroform/methanol: 9.5/0.5) allows the expected product to be isolated.

Step B: [(2-{[(Benzyloxy)carbonyl]amino}-3-{4-[(tert-butoxycarbonyl)oxy]phenyl}-propanoyl)oxy]methyl pivalate To a solution of 2.5 mmol of the compound of Step A above in 15 ml of chloroform there are added $(nBu)_4NHSO_4$ (0.5 of an equivalent), triethylamine (2 equivalents), sodium iodide (1 equivalent) and chloromethyl pivalate (2 equivalents). The reaction mixture is refluxed for 18 hours and then concentrated. The residue is dissolved in diethyl ether and is extracted with water, twice with 0.5M HCl, twice with 5% $NaHCO_3$, and with water. The organic phase is concentrated and chromatography (dichloromethane/methanol: 9.9/0.1 to 9.5/0.5) allows the expected product to be isolated.

Step C: [(2-Amino-3-{4-[(tert-butoxycarbonyl)oxy]phenyl}propanoyl)oxy]methyl 2,2-dimethylpropanoate hydrochloride 2 mmol of the compound of Step B above are dissolved in a mixture (2/1) of ethanol/water, and a few drops of 0.5M HCl are added until a pH of 1 is reached. The reaction mixture is hydrogenated with the aid of a hydrogen flask in the presence of Pd/C (300 mg) as catalyst. After 2.5 hours, the mixture is filtered over Celite and is then evaporated to dryness to obtain the expected product.

Step D: (5R,8*,11S)-5-Benzyl-11-{4-[(tert-butoxycarbonyl)oxy]benzyl}-3.9,12,16-tetraoxo-1-phenyl-8-[(3-phenyl-5-isoxazolyl)methyl]-2,13,15-trioxa-4,10-diaza-17,17-dimethyloctadecane-6-phosphinic acid To a suspension of 1.3 mmol of the compound of Preparation 3 in 7 ml of dichloromethane there are added 3 equivalents of diisopropylethylamine, 1 equivalent of the compound of Step C above, 1 equivalent of HOBt and 5 equivalents of EDC.HCl. The reaction mixture is stirred for 75 minutes and is then concentrated under reduced pressure. The residue is dissolved in 50 ml of a mixture (9/1) of ethyl acetate/diethyl ether and is then extracted four times with 1M HCl, $H_2O$, three times with 5% $NH_4HCO_3$, $H_2O$, twice with 5% $NaHCO_3$, $H_2O$, 1M HCl and then brine. The organic phase is concentrated and chromatography (chloroform/methanol/acetic acid: 9.5/0.4/0.1) allows the expected product to be isolated.

Step E: (5R,8*,11S)-5-Benzyl-11-(4-hydroxybenzyl)-3,9,12,16-tetraoxo-1-phenyl-8-[(3-phenyl-5-isoxazolyl)methyl]-2,13,15-trioxa-4,10-diaza-17,17-dimethyloctadecane-6-phosphinic acid 1 mmol of the compound of Step D above is dissolved in 10 ml of formic acid and 200 µl of triisopropylsilane. The reaction mixture is stirred at ambient temperature for 50 minutes and is then concentrated under reduced pressure. The residue is dissolved in ethyl acetate and extracted twice with brine, twice with 5% $NaHCO_3$, brine, 1M HCl and brine. The organic phase is concentrated to yield the expected product.

Mass spectrometry (MS-ESI)=826.3 $(M+H)^+$

EXAMPLE 5

(5R,8*,11S)-5-Benzyl-11-(4-hydroxybenzyl)-3,9,12-trioxo-1-phenyl-8-[(3-phenyl-5-isoxazolyl)methyl]-2,13-dioxa-4,10-diaza-pentadecane-6-phosphinic acid Step A: 2-{[(Benzyloxy)carbonyl]amino}-3-{4-[(tert-butoxycarbonyl)oxy]phenyl}ethyl propanoate To a solution of 4 mmol of the compound of Step A of Example 4 in 5 ml of absolute ethanol there are added HOBt (1.1 equivalents), EDC.HCl (1.1 equivalents), DMAP (catalytic amount) and DIPEA (1.1 equivalents). The reaction mixture is stirred at ambient temperature for 18 hours and is then concentrated. The residue is dissolved in diethyl ether, and is extracted with water, twice with 0.5M HCl, twice with 5% $NaHCO_3$ and with water. The aqueous phase is dried over $Na_2SO_4$ and is then concentrated to yield the expected product.

Step B: 2-Amino-3-{4-[(tert-butoxycarbonyl)oxy]phenyl}ethyl propanoate hydrochloride The product is obtained in accordance with the procedure of Step C of Example 4, using the compound of Step A above.

Step C: (5R,8*,11S)-5-Benzyl-11-{4-[(tert-butoxycarbonyl)oxy]benzyl}-3,9,12-trioxo-1-phenyl-8-[(3-phenyl-5-isoxazolyl)methyl]-2,13-dioxa-4,10-diaza-pentadecane-6-phosphinic acid The product is obtained in accordance with the procedure of Step D of Example 4, using the compound of Step B above.

Step D: (5R,8*,11S)-5-Benzyl-11-(4-hydroxybenzyl)-3,9,12-trioxo-1-phenyl-8-[(3-phenyl-5-isoxazolyl)methyl]-2,13-dioxa-4,10-diaza-pentadecane-6-phosphinic acid The product is obtained in accordance with the procedure of Step E of Example 4, using the compound of Step C above.

Mass spectrometry (MS-ESI)=740.2 $(M+H)^+$

EXAMPLE 6

(5R,8*,11S)-5-Benzyl-11-(4-hydroxybenzyl)-3,9,12,17-tetraoxo-1,17-diphenyl-8-[(3-phenyl-5-isoxazolyl)methyl]-2,13-dioxa-4,10-diaza-16-thiaheptadecane-6-phosphinic acid Step A: 2-(Benzoylsulphanyl)-3-(4-tert-butoxyphenyl)-2-{[(9H-fluoren-9-ylmethoxy)carbonyl]amino}ethyl propanoate The compound is obtained in accordance with the procedure of Step A of Example 5, using FmocTyr (OBu$^t$)(OH) instead of the compound of Step A of Example 4 and using PhCOSCH$_2$CH$_2$OH (described in the literature I. Lefebvre et al., J. Med. Chem., 1995, 38, 3941-3950) instead of absolute ethanol in dichloromethane.

Step B: 2-(Benzoylsulphanyl)-2-amino-3-(4-tert-butoxyphenyl)ethyl propanoate 1.5 mmol of the compound of Step A above are dissolved in 12 ml of dimethylformamide and 3 equivalents of diethylamine. The reaction mixture is stirred at ambient temperature for 1 hour and is then concentrated under reduced pressure. The residue is dissolved in ethyl acetate and is extracted three times with water and with brine. Chromatography (chloroform/methanol: 9.5/0.5) and then precipitation from a mixture (2/1) of petroleum ether/diethyl ether allows the expected product to be isolated.

Step C: (5R,8*,11S)-5-Benzyl-11-(4-tert-butoxybenzyl)-3,9,12,17-tetraoxo-1,17-diphenyl-8-[(3-phenyl-5-isoxazolyl)methyl]-2,13-dioxa-4,10-diaza-16-thiaheptadecane-6-phosphinic acid The product is obtained in accordance with the procedure of Step D of Example 4, using the compound of Step B above.

Step D: (5R,8*,11S)-5-Benzyl-11-(4-hydroxybenzyl)-3,9,12,17-tetraoxo-1,17-diphenyl-8-[(3-phenyl-5-isoxazolyl)methyl]-2,13-dioxa-4,10-diaza-16-thiaheptadecane-6-phosphinic acid The product is obtained in accordance with the procedure of Step E of Example 4, using the compound of Step C above.
Mass spectrometry (MS-ESI)=874.3 (M−H)$^−$

EXAMPLE 7

(5R,8*,11S)-5-Benzyl-11-4-(tert-butoxybenzyl)-6-[2(ethanethioate)ethoxy]-3,9-dioxo-1-phenyl-8-[(3-phenyl-5-isoxazolyl)methyl]-2-oxa-4,10-diaza-6-phosphadodecan-12-oic acid 6-oxide Step A: (5R,8*,11S)-5-Benzyl-11-(4-tert-butoxybenzyl)-3,9,12-trioxo-1-phenyl-8-[(3-phenyl-5-isoxazolyl)methyl]-2,13-dioxa-4,10-diaza-14,14-dimethylpentadecane-6-phosphinic acid The product is obtained in accordance with the procedure of Step D of Example 4, using the compound of Preparation 3 and HCl.HTyr(OBu$^t$)OBu$^t$.

Step B: tert-Butyl (5R,8*,11S)-5-benzyl-11-4-(tert-butoxybenzyl)-6-[2(ethanethioate)ethoxy]-3,9-dioxo-1-phenyl-8-[(3-phenyl-5-isoxazolyl)methyl]-2-oxa-4,10-diaza-6-phosphadodecan-12-oate 6-oxide 0.36 mmol of the compound of Step A above is dissolved in 4 ml of dimethylformamide and there are then added 3 equivalents of DIPEA, 3 equivalents of CH$_3$COSCH$_2$CH$_2$OH (I. Lefebvre et al., J. Med. Chem., 1995, 38, 3941-3950) and 3 equivalents of P$_y$POB. The reaction mixture is stirred at ambient temperature for 48 hours and is then diluted with ethyl acetate. The organic phase is extracted four times with 1M HCl, H$_2$O, three times with 5% NH$_4$HCO$_3$, twice with 1M HCl and then brine. The organic phase is dried and is then concentrated. Chromatography (chloroform/methanol: 9.8/0.2) allows the expected product to be isolated.

Step C: (5R,8*,11S)-5-Benzyl-11-4-(tert-butoxybenzyl)-6-[2(ethanethioate)ethoxy]-3,9-dioxo-1-phenyl-8-[(3-phényl-5-isoxazolyl)methyl]-2-oxa-4,10-diaza-6-phosphadodecan-12-oic acid-6-oxide The product is obtained in accordance with the procedure of Step E of Example 4, using the compound of Step B above.
Mass spectrometry (MS-ESI)=814.3 (M+H)$^+$

EXAMPLE 8

Ethyl (5R,8*,11S)-5-benzyl-6-ethoxy-11-(4-hydroxybenzyl)-3,9-dioxo-1-phenyl-8-[(3-phenyl-5-isoxazolyl)methyl]-2-oxa-4,10-diaza-6-phosphadodecan-12-oate 6-oxide Step A: Ethyl (5R,8*,11S)-5-benzyl-11-{4-[(tert-butoxycarbonyl)oxy]benzyl}-6-ethoxy-3,9-dioxo-1-phenyl-8-[(3-phenyl-5-isoxazolyl)methyl]-2-oxa-4,10-diaza-6-phosphadodecan-12-oate 6-oxide The product is obtained in accordance with the procedure of Step B of Example 7, using the compound of Step C of Example 5 and ethanol.

Step B: Ethyl (5R,8*,11S)-5-benzyl-6-ethoxy-11-(4-hydroxybenzyl)-3,9-dioxo-1-phenyl-8-[(3-phenyl-5-isoxazolyl)methyl]-2-oxa-4,10-diaza-6-phosphadodecan-12-oate 6-oxide The product is obtained in accordance with the procedure of Step E of Example 4, using the compound of Step A above.
Mass spectrometry (MS-ESI)=768.3 (M+H)$^+$;790.3 (M+Na$^+$)$^+$

EXAMPLE 9

Ethyl (5R,8*,11S)-5-benzyl-11-(4-hydroxybenzyl)-6-[2-methyl-1-(propionyloxy)propoxy]-3,9-dioxo-1-phenyl-8-[(3-phenyl-5-isoxazolyl)methyl]-2-oxa-4,10-diaza-6-phosphadodecan-12-oate 6-oxide Step A: Ethyl (5R,8*,11S)-5-benzyl-11-{4-[(tert-butoxycarbonyl)oxy]benzyl}-6-[2-methyl-1-(propionyloxy)propoxy]-3,9-dioxo-1-phenyl-8-[(3-phenyl-5-isoxazolyl)methyl]-2-oxa-4,10-diaza-6-phosphadodecan-12-oate 6-oxide The product is obtained in accordance with the procedure of Step B of Example 7, using the compound of Step C of Example 5 and BrCH(CH(CH$_3$)$_2$)OCOEt (M. Neuenschwander et al., Helv. Chim. acta, 1978, 61, 2047-2058).

Step B: Ethyl (5R,8*,11S)-5-benzyl-11-(4-hydroxybenzyl)-6-[2-methyl-1-(propionyloxy)propoxy]-3,9-dioxo-1-phenyl-8-[(3-phenyl-5-isoxazolyl)methyl]-2-oxa-4,10-diaza-6-phosphadodecan-12-oate 6-oxide The product is obtained in accordance with the procedure of Step E of Example 4, using the compound of Step B above.
Mass spectrometry (MS-APCI)=868.4 (M+H)$^+$; 885.5 (M+NH$_4^+$)$^+$

EXAMPLE 10

(5R,8*,11S)-5-Benzyl-11-(4-hydroxybenzyl)-6-[2-methyl-1-(propionyloxy)-propoxy]-3,9-dioxo-1-phenyl-8-[(3-phenyl-5-isoxazolyl)methyl]-2-oxa-4,10-diaza-6-phosphadodecan-12-oic acid 6-oxide Step A: tert-Butyl (5R,8*,11S)-5-benzyl-11-(4-tert-butoxybenzyl)-6-[2-methyl-1-(propionyloxy)propoxy]-3,9-dioxo-1-phenyl-8-[(3-phenyl-5-isoxazolyl)methyl]-2-oxa-4,10-diaza-6-phosphadodecan-12-oate 6-oxide The product is obtained in accordance with the procedure of Step A of Example 9, using the compound of Step A of Example 7 instead of the compound of Step C of Example 5.
Mass spectrometry (MS-ESI)=974.5 (M+Na$^+$)$^+$ Step B: (5R,8*,11S)-5-Benzyl-11-(4-hydroxybenzyl)-6-[2-methyl-1-(propionyloxy)propoxy]-3,9-dioxo-1-phenyl-8-[(3-phenyl-5-isoxazolyl)methlyl]-2-oxa-4,10-diaza-6-phosphadodecan-12-oic acid 6-oxide The product is obtained in accordance with the procedure of Step E of Example 4, using the compound of Step A above.
Mass spectrometry (MS-ESI)=838.5 (M−H)$^−$

PHARMACOLOGICAL STUDY OF COMPOUNDS OF THE INVENTION

EXAMPLE A

In vitro inhibitory effect on angiotensin converting enzyme (ACE) and endothelin converting enzyme (ECE)

In order to compare their specificity, the compounds of the Examples were tested on 2 enzymes: ACE (recombinant human form) and ECE (recombinant human form of the isoform ECE-1c).

The tests were carried out in duplicate in 96-well plates. The inhibitor was incubated together with the enzyme for 45 minutes before the addition of a quenched-fluorescence substrate. The fluorescence emitted was detected and measured in a Fluoroscan Ascent plate reader (Thermo-Labsystems).

The fluorogenic substrates used are: Mca-Arg-Pro-Pro-Gly-Phe-Ser-Pro-Dpa$_{COOH}$ (5 µM) with ACE, and Mca-Arg-Pro-Pro-Gly-Phe-Ser-Ala-Phc-Lys(Dnp)$_{COOH}$ (5 µM; R&D Systems) with ECE.

The compounds of the invention show good inhibition of ACE and of ECE, with IC$_{50}$ values of 25 nM and 8 nM respectively.

The results obtained are collated in the following Table:

| Compound | IC$_{50}$ (nM) | |
| --- | --- | --- |
|  | ACE | ECE |
| Example 1 | 36 | 8 |
| Example 2 | 3.8 | 7.7 |
| Example 3 | 1.4 | 1.4 |

EXAMPLE B

| Pharmaceutical composition | |
| --- | --- |
| 1000 tablets each comprising 5 mg of the compound of Example 1 | 5 g |
| wheat starch | 20 g |
| maize starch | 20 g |
| lactose | 30 g |
| magnesium stearate | 2 g |
| silica | 1 g |
| hydroxypropylcellulose | 2 g |

The invention claimed is:
1. A compound selected from those of formula (I):

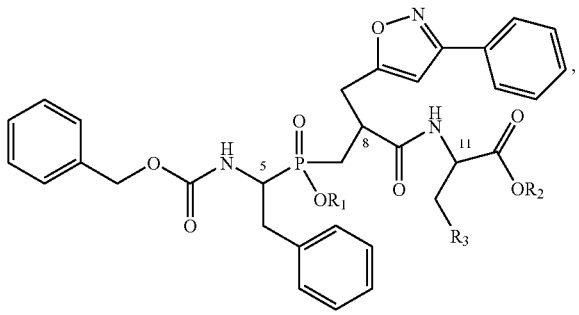

wherein:
R$_1$ represents a hydrogen atom, a (C$_1$-C$_6$)alkyl-carbonyloxy-(C$_1$-C$_6$)alkyl group in which the alkyl moiety may be linear or branched, or a (C$_1$-C$_6$)alkyl-carbonylthio-(C$_1$-C$_6$)alkyl group in which the alkyl moiety may be linear or branched, R$_2$ represents a hydrogen atom, a (C$_1$-C$_6$)alkyl-carbonyloxy-(C$_1$-C$_6$)alkyl group in which the alkyl moiety may be linear or branched, an arylcarbonylthio-(C$_1$-C$_6$)alkyl group in which the alkyl moiety may be linear or branched, or an aryl-(C$_1$-C$_6$)alkyl group in which the alkyl moiety may be linear or branched and the aryl moiety may be optionally substituted by a (C$_1$-C$_6$)alkyl-carbonyloxy group, R$_3$ represents a phenyl group, optionally substituted by a hydroxy group, or 3-indolyl group, or R$_1$ may also represent a linear or branched (C$_1$-C$_6$)alkyl group and R$_2$ represents a linear or branched (C$_1$-C$_6$) alkyl group, when R$_3$ represents a phenyl group substituted by a hydroxy group, its enantiomers and diastereoisomers, and addition salts thereof with a pharmaceutically acceptable base.

2. The compound of claim 1, wherein $R_1$ and $R_2$ each represent a hydrogen atom.

3. The compound of claim 1, wherein $R_1$ represents a hydrogen atom and $R_3$ represents a phenyl group substituted by a hydroxy group.

4. The compound of claim 1, wherein $R_2$ represents a hydrogen atom and $R_3$ represents a phenyl group substituted by a hydroxy group.

5. The compound of claim 1, which is selected from:
(5R,8R,11S)-5-benzyl-6-hydroxy-11-(1H-indol-3-ylmethyl)-3,9-dioxo-1-phenyl-8-[(3-phenyl-5-isoxazolyl)methyl]-2-oxa-4,10-diaza-6-phosphadodecan-12-oic acid 6-oxide,
(5R,8R,11S)-5,11-dibenzyl-6-hydroxy-3,9-dioxo-1-phenyl-8-[(3-phenyl-5-isoxazolyl)-methyl]-2-oxa-4,10-diaza-6-phosphadodecan-12-oic acid 6-oxide,
(5R,8R,11S)-5-benzyl-6-hydroxy-11-(4-hydroxybenzyl)-3,9-dioxo-1-phenyl-8-[(3-phenyl-5-isoxazolyl)methyl]-2-oxa-4,10-diaza-6-phosphadodecan-12-oic acid 6-oxide, its enantiomers and diastereo isomers, and addition salts thereof with a pharmaceutically acceptable base.

6. A pharmaceutical composition comprising as active ingredient at least one compound of claim 1, in combination with one or more pharmaceutically acceptable, inert, non-toxic excipients or carriers.

7. A method of treating a living animal body, including a human, afflicted with a condition selected from arterial hypertension, pulmonary arterial hypertension, and diabetic retinopathies comprising the step of administering to the living animal body, including a human, an amount of a compound of claim 1 which is effective for treatment of the condition.

* * * * *